United States Patent [19]
Lawlor

[11] Patent Number: 5,623,947
[45] Date of Patent: Apr. 29, 1997

[54] DEVICE TO BE USED WITH CONDOMS TO PREVENT THE TRANSMISSION OF DISEASE

[76] Inventor: Kevin B. Lawlor, 493 Arborway, Jamaica Plain, Mass. 02130

[21] Appl. No.: 297,596

[22] Filed: Aug. 29, 1994

[51] Int. Cl.⁶ ........................................................ A61F 5/44
[52] U.S. Cl. ........................... 128/844; 128/918; 604/352
[58] Field of Search ................................... 128/842, 844, 128/918; 604/330, 347–353

[56] References Cited

U.S. PATENT DOCUMENTS

| | | | |
|---|---|---|---|
| 2,348,773 | 5/1944 | Wyman | 128/844 |
| 4,794,920 | 1/1989 | Robichaud | 128/844 |
| 4,856,534 | 8/1989 | Sorkin et al. | 128/844 |
| 4,869,269 | 9/1989 | Sharkan | 128/844 |
| 4,945,923 | 8/1990 | Evans | 128/844 |
| 4,955,392 | 9/1990 | Sorkin | 128/844 |
| 4,976,273 | 12/1990 | Hessel | 128/844 |
| 5,083,414 | 1/1992 | Wu | 128/844 |
| 5,351,699 | 10/1994 | Hammons | 128/844 |

FOREIGN PATENT DOCUMENTS

| | | | |
|---|---|---|---|
| 0429144 | 5/1991 | European Pat. Off. | 128/918 |
| 2226957 | 7/1990 | United Kingdom | 128/918 |

*Primary Examiner*—Sam Rimell
*Attorney, Agent, or Firm*—Jerry Cohen; Jacob N. Erlich

[57] ABSTRACT

A flexible shield made of material that prevents through transmission of fluids. The shield is constructed with a through hole and tubular portion extending normal to the shield surface. The tubular portion is designed to fit at the base of the penis with the shield laying over the pubic area adjacent to the penis. The tubular portion is designed to fit at the base of the penis with the shield laying over the pubic area adjacent to the penis. The tubular portion is designed to adhere to the penis and to matingly accept the end of a condom unrolled over the penis. The part of the tube that contacts the condom may be ripple to secure the condum during the inward or lateral stress motions associated with sexual activity.

4 Claims, 4 Drawing Sheets

20

DEVICE TO BE USED WITH CONDOMS TO PREVENT THE TRANSMISSION OF DISEASE

BACKGROUND OF THE INVENTION

There is concern about sexually transmitted diseases, referred to as STDs. STDs an be contracted through contact with another person during sexual intercourse and related activities. STDs are usually transmitted through skin to skin contact and or the exchange of bodily fluids including; blood, semen, vaginal fluids, feces and urine during sexual intercourse and related activities.

During sexual intercourse STDs are primarily transmitted through contact of parts of the male anatomy that includes, the penis and surrounding pubic area and of the female anatomy that includes the vagina, the interior and exterior portions of the labia and surrounding pubic areas. STDs can be transmitted through contact in and around the anus of both males and females. There are devices, such as condoms, which are put on the erect penis and if used properly, provide some protection from the exchange of certain bodily fluids, such as semen, during sexual intercourse and related activities. Condoms also provide a limited barrier from skin to skin contact in the areas covered by the condom during sexual intercourse and related activities. This condom provides a barrier between the penis and the interior portions of the female vagina during sexual intercourse.

A condom provides a barrier from skin to skin contact during anal and vaginal intercourse. Surrounding areas not covered by the condom would be liable to incur skin to skin contact during anal and vaginal intercourse.

However, condoms are designed as a contraceptive device to entrap the male sperm within it and not allow it to encounter the female vagina during sexual intercourse, the result of this encounter being the prevention of insemination. Thus this entrapment prevents the male sperm from impregnating the female partner while the penis is inside the female vagina during sexual intercourse.

Condoms are used to prevent the transmission of STDs during sexual intercourse and related activities. However, they are not specifically designed for that purpose. However within the areas of the penis they cover and the parts of the female vagina they encounter they do prevent skin to skin contact. If the penis does not enter the vagina beyond the end of the condom it is unlikely that bodily fluids would be exchanged.

However condoms are not designed for the purpose of preventing skin to skin contact during sexual intercourse. They are also not designed to prevent the exchange of bodily fluids, with the exception of semen, during sexual intercourse and related activities. During sexual intercourse and related activities although a condom may be worn it is unlikely that skin to skin contact of the genitalia of the partners would not occur. It is also unlikely that certain bodily fluids such as vaginal fluid would not be exchanged during sexual intercourse even if a condom was properly employed.

Because they are not designed for the purpose of preventing skin to skin contact and preventing the exchange of bodily fluids during sexual intercourse the transmission of STDs might occur because of the aforementioned contact and exchange. This contact and or exchange could occur in areas of the genitalia not covered by the condom during sexual intercourse and related activities. Our invention pertains to these areas of the genitalia in the male and female not covered by the condom during sexual intercourse and related activities.

The transmission of certain STDs does occur from skin to skin contact and the exchange of bodily fluids during sexual intercourse and related activities even when a condom is properly employed. Herpes II or genital herpes is often transmitted from skin to skin contact and the exchange of bodily fluids during sexual intercourse even when a properly employed condom is used.

Although condoms do provide a barrier to portions of the penis and protection to portions of the female vagina during sexual intercourse and related activities, skin to skin contact and the exchange of bodily fluids does occur even when a condom is properly used.

The condom is limited in its ability to cover the base of the penis. The condom further does not protect or cover the areas immediately surrounding the male and female genitalia during sexual intercourse and related activities.

When a condom is used during sexual intercourse, there exists the possibility of bodily fluids leaking from the condom and onto the partner's skin.

All of the above limitations of the existing devices could result in skin to skin contact and or the exchange of bodily fluids during sexual intercourse and related activities.

Even if the condom were made exceptionally long and unrolled as far up the penis toward the base end as possible, there still exists the possibility of skin to skin contact in the pubic area of the male and female during sexual intercourse and related activities. There also exists the potential for the exchange of bodily fluids from the female labia and or pubic area and or any lesions or sores on the male at the base end of the penis and surrounding pubic area during sexual intercourse and related activities.

It is a further limitation of condoms, when used to prevent the contracting of STDs that STDs are transmitted by males and females from skin to skin contact and through the exchange of bodily fluids in the genital areas and immediately surrounding pubic areas not covered by condoms during sexual intercourse and related activities.

SUMMARY OF THE INVENTION

There are many STDs. Herpes II or genital Herpes is transmitted from one person to another through skin to skin contact. In a common form of infection the skin of the infected person contains a lesion in which the Herpes virus is present. The soon to be infected persons skin contacts this area. The most easily infected areas are those with the fewest layers of skin covering, such as the genitals.

Herpes II or Genital Herpes outbreaks can last from five to ten-days and can occur as often as once a month. Herpes II or Genital Herpes can be transmitted before, during and after an outbreak. Herpes virus is present in lesions that occur on the skin in and around the genital areas and anus of the infected male and female. In a common form of infection the virus is passed on during the prodomal phase of an outbreak before the infected person realizes an outbreak is about to occur. This prodomal phase shows no visible lesions and no other symptoms are present. Another way Herpes II is contracted is through "Asymptomatic shedding" which occurs 3 or 4 days a year in the infected. Condoms alone do not prevent transmission of the disease. Condoms only cover about three quarters of the shaft of penis. They are designed to entrap male sperm, not completely cover the penis. When using a condom the base of the penis shaft and the area immediately surrounding that base are uncovered. During sexual intercourse skin to skin contact would result in those uncovered areas. If lesions were present, for example Herpes II lesions, on the penis in these areas or if they were present on female genitals encountering these areas, Herpes II could be transmitted. This transmission could be from an infected male to a female or an infected female to a male. Infection could also occur if Herpes II lesions were present in the pubic area immediately surrounding the penis in the male and the vagina in the female partner.

The foregoing objects are met in a new device which is a protective shield comprising a tube with both ends open. This tube is attached to and part of as one unit a diaphragm with a through hole attached to one end of the tube, The tube and diaphragm are diametrically on the same central axis.

It is further understood that the tube would extend out from the diaphragm far enough to allow an average length condom to overlap it by enough distance to create a reasonable seal between the condom and our device.

It is further met by the abovementioned diaphragm being flexible. The flexibility of the tube as well (the tube and diaphragm are one unit and hence made from the same material) allows it to be covered by and take on the shape of the condom that covers it and thereby create a reasonable barrier and seal from skin to-skin contact and the exchange of bodily fluids respectively. The flexibility of the material should allow the aforementioned barrier and seal to remain intact as one unit during the movement and abrasion encountered by the device and condom during sexual intercourse and related activities.

It is further met by the combination of the condom and the device creating a protective barrier from skin to skin contact and creating a seal at the point of overlap between condom and our device to prevent the exchange of bodily fluids during sexual intercourse and related activities. The seal between the condom and the device would rely on an adequate amount of overlapping of the two in order to prevent whatever bodily fluids that did leak down the base end of the condom from preceding past the open tubular end of our device and onto the skin of the partner during sexual intercourse and related activities.

It is further met by a tube with a diaphragm at the end of the tube that does not enter the vagina during sexual intercourse and related activities although it is properly employed with a condom. The aforementioned diaphragm flares out at the base of the penis to protect and cover the surrounding pubic area in the male and to present a barrier from contact with the pubic area surrounding the vagina in the female during sexual intercourse and related activities, The aforesaid diaphragm would extend outward in a flat plane in all directions from the central axis, the same axis as the penis and tube. The diaphragm would extend outward to such an extent that it would cover the area at the base of the penis and surrounding pubic area and present a barrier to the female labia and surrounding pubic area, these male and female areas can be infected and therefore transmit STDs if uncovered. This flexible diaphragm is a portion of the device that is not covering the penis or entering the vagina during sexual intercourse and related activities, but acts as a barrier or shield between male and female body parts immediately surrounding and exterior to the penis and vagina and hence prevents skin to skin contact in these areas and the transmission of bodily fluids around the diaphragm and into the tube portion of the device and further down the condom during sexual intercourse and related activities.

It is a further object of the invention in combination with a condom to provide a barrier and a protective shield in a single unit which covers the entire penis, base of the penis and surrounding pubic areas in the male during sexual intercourse and related activities and thereby creating a barrier to corresponding areas in the female partner such as the vagina, labia and surrounding pubic area.

Other objects, features and advantages will be apparent from the following detailed description of preferred embodiments taken in conjunction with the accompanying drawings in which:

DETAILED DESCRIPTION OF PREFERRED EMBODIMENTS

Figure 1:
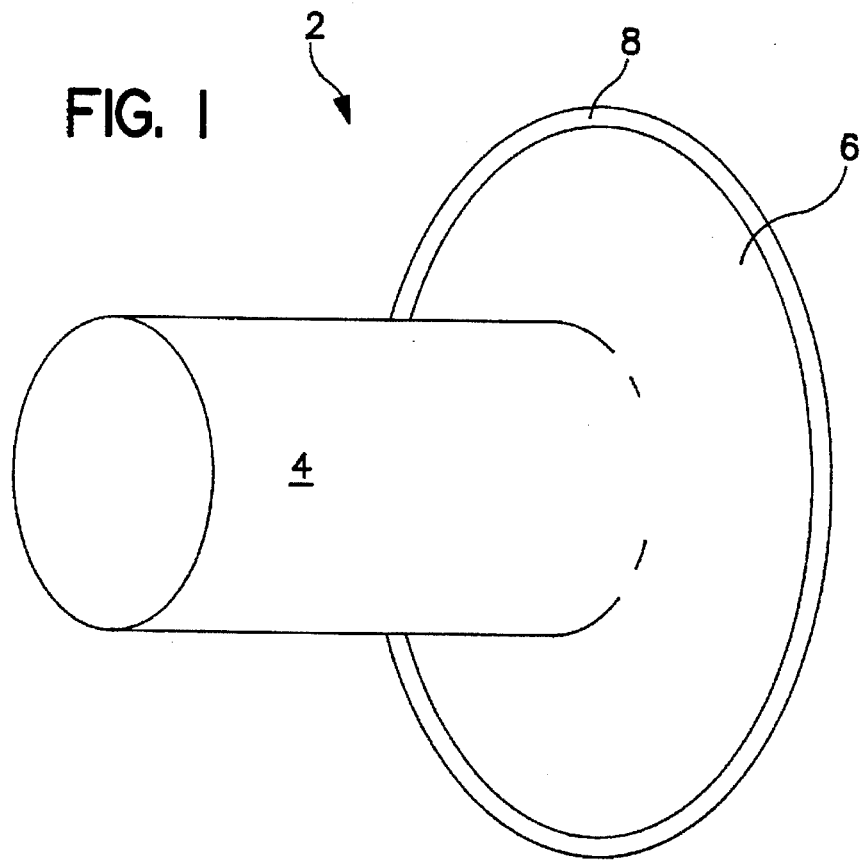
FIG. 1 is a preferred embodiment of the device in three-quarter sideview.

FIG. 1 shows (-in three-quarter side view) device 2, made in accordance with the present invention, for protection from the transmission of STDs when worn with a condom on the penis during sexual intercourse and related activities. The device consists of a circular tube 4 with both ends open. Attached to end of the tube is a circular diaphragm 6 extending radially from the tube end. At the circumference of the diaphragm there is a ring 8. This ring can be flexed, however, the ring reverts to the circular shape (as shown in FIG. 1), when unflexed.

FIG. 1 shows the tube portion and the diaphragm portion fabricated as one unit. The device may be made of a flexible rubberlike material the same, compatible and or similar to that of the condom used with it. This compatibility of materials and circular shape and close circumferential diameter allows the condom and the device to take on the circumferential shape of each other and create a seal at the overlapping area while on the erect penis during sexual intercourse and related activities. Further the material of the device could be made of a version of the aforementioned material of the condom. A thicker version, at the same density, would be more durable than the condom. This increased thickness of material could be possible because the portion of the penis covered by the device does not rely on as much sensitivity to what it encounters as that portion of the penis covered by the condom. The device would be made of a material that prevents the through transmission of fluids.

In order to use the device it would be held in both hands at the diaphragm end. The tube end, distal from the diaphragm end, would be pointing outward in the same direction as the erect penis. The empty tube at the diaphragm end is slid over the erect penis and slipped down the shaft until the tube at the diaphragm end is as far down the base end of the penis as possible. The diaphragm would encounter the pubic area of the male at the side of the diaphragm opposite that of the length of tube of the device. The device would be slipped, over the erect penis before the occurrence of skin to skin contact with a partner and as a prelude to sexual intercourse and related activities. After the aforementioned device is put on the erect penis, but again before skin to skin contact occurs between partners, the condom 16 is employed. The properly employed condom is completely unrolled over the erect penis, down the penis shaft, and over the inventive device. The condom, therefore, covers and overlaps the tube portion of our device from one end of the tube to the other. In other words, the condom begins overlapping our device at the non-diaphragm end and overlaps the tube all the way to the end that encounters the diaphragm.

Figure 2:
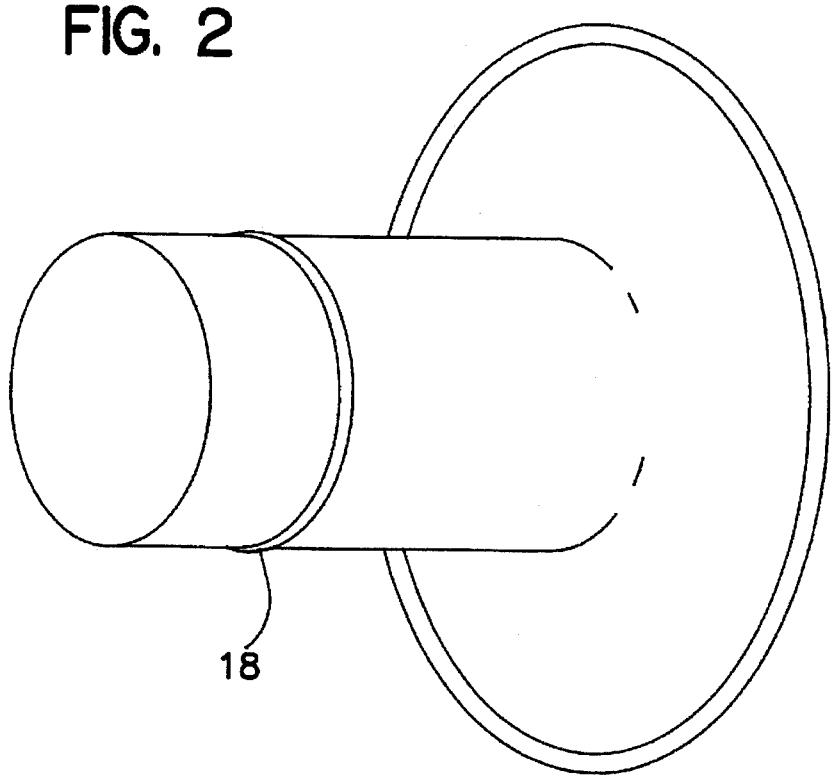
FIG. 2 is another preferred embodiment showing a raised portion of material or a narrow ringlike rise at one point in the tube portion of the device.
Figure 4:
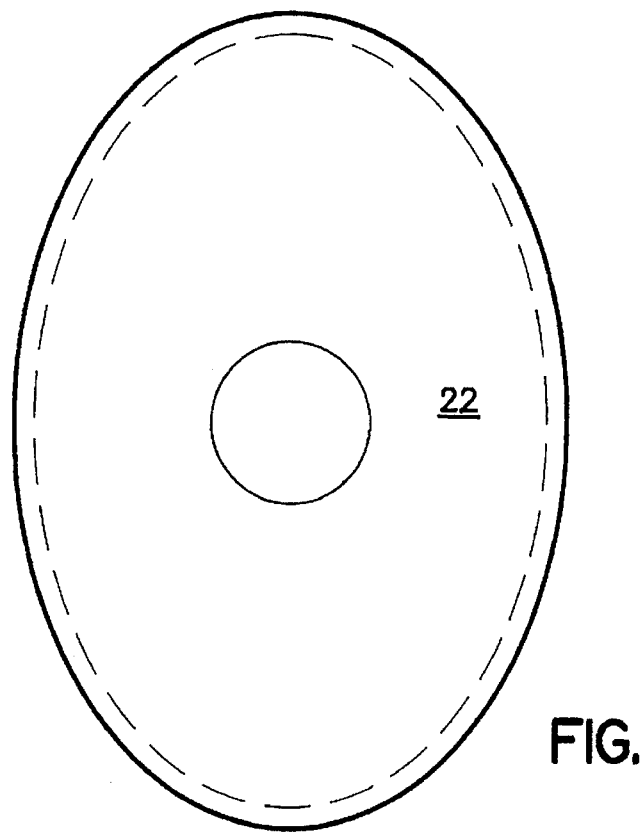
FIG. 4 is a preferred embodiment of the device in a front plan view with an elliptical diaphragm.
Figure 5:
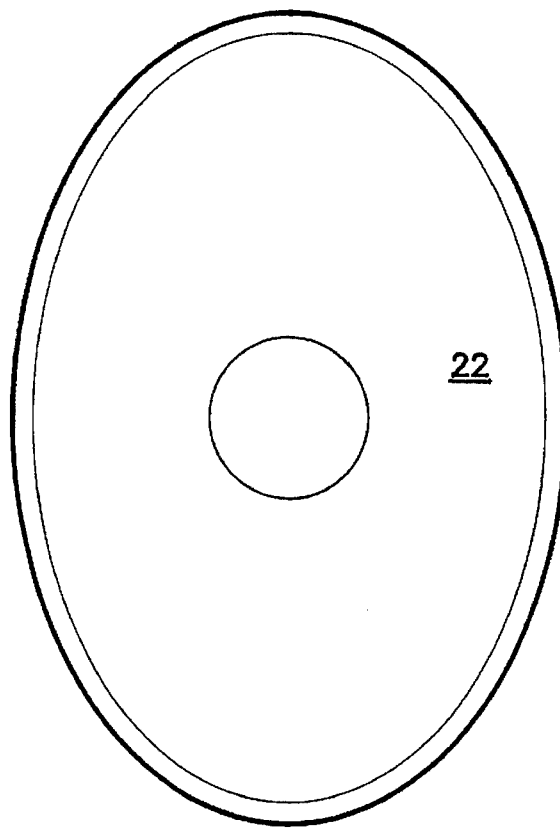
FIG. 5 is a rear view of the preferred embodiment from FIG. 4.

FIGS. 4 and 5 clearly depict areas of adhesion on tube 4 of the inventive device 2 which are constructed to secure condom 16 thereto. More specifically, FIG. 2 is another preferred embodiment of the device with a raised portion 18 of material or a narrow ringlike rise at one point in the tube portion of the device. This ring raises the circumferential diameter of the tube in that area. The accompanying condom would be unrolled beyond this area and overlap it. The ring at the end of the unrolled condom, once unrolled over the raised ring on our device, would be unlikely to increase in diameter and unroll back over the raised ring of our device during movement and abrasion at the time of sexual intercourse and related activities.

Figure 3:
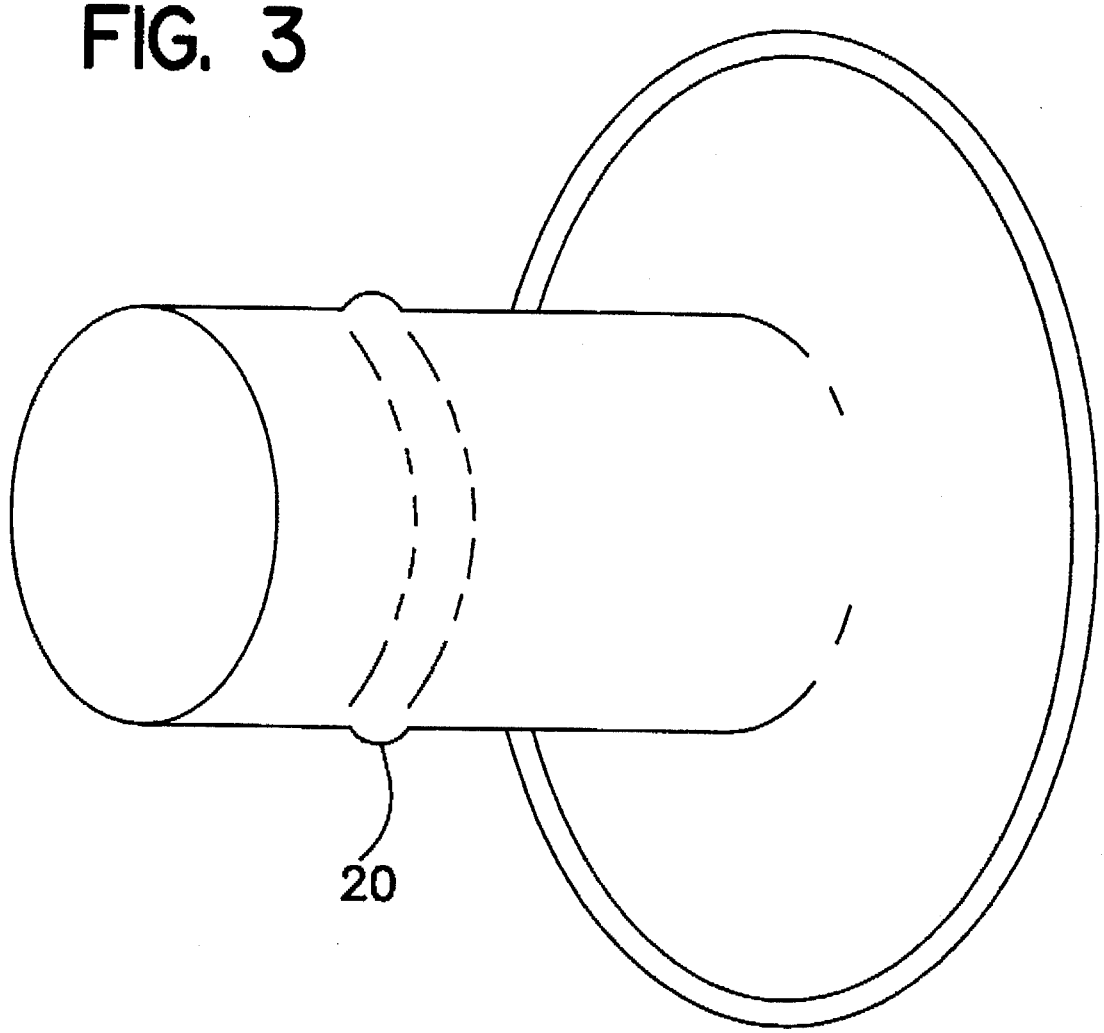
FIG. 3 is another preferred embodiment with a different type of raised portion similar to that in FIG. 2.

FIG. 3 shows a different type of raised portion 20 similar to that in FIG. 2. This raised portion is an enlarged circumferential ripple in a narrow area in the tube portion of the device.

FIG. 4 shows a preferred embodiment of the device in a front plan view with an elliptical diaphragm 22.

FIG. 5 shows a rear view of the preferred embodiment from FIG. 4.

Figure 6:
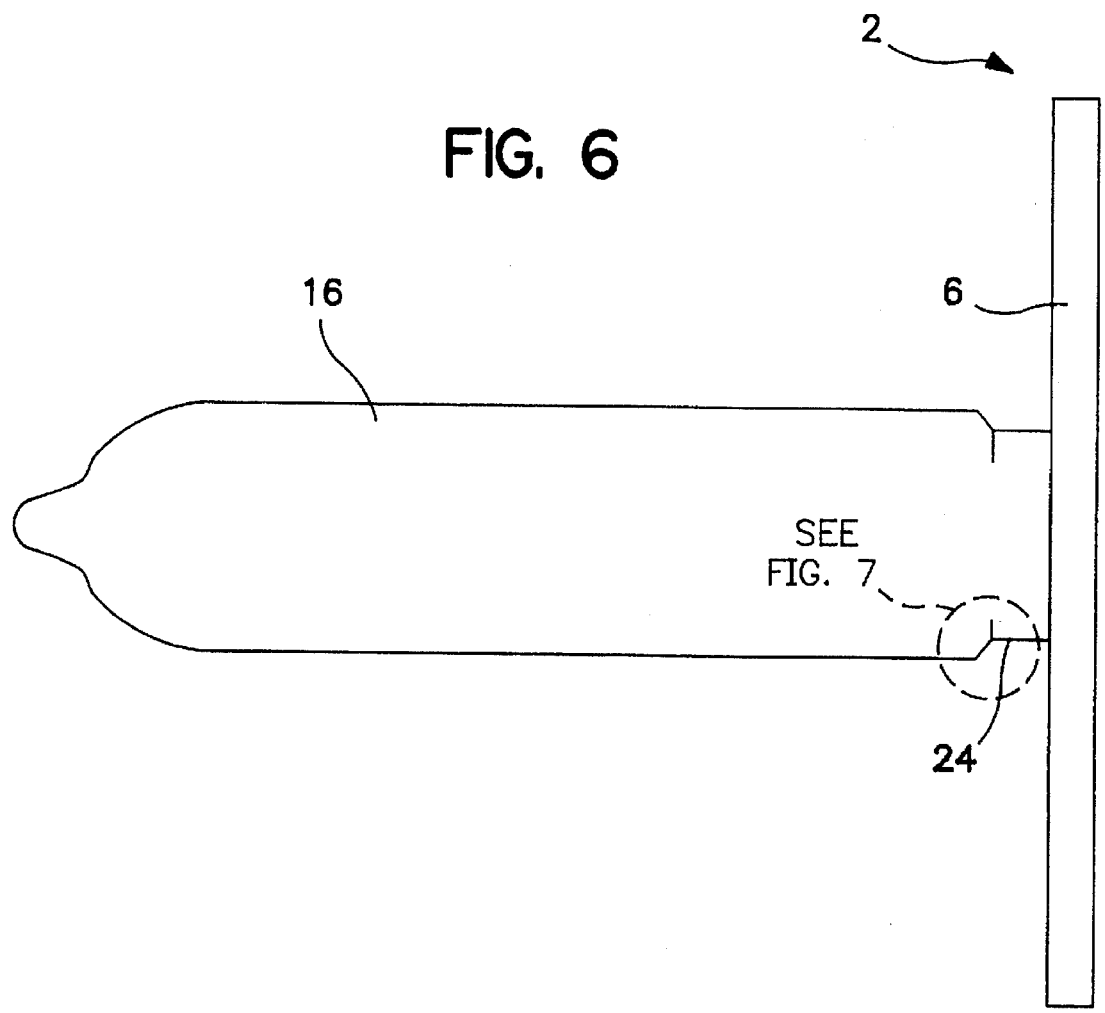
FIG. 6 is a sideview of as one unit a condom and a diaphragm.

FIGS. 8 and 9 clearly depict areas of adhesion on tube 4 of the inventive device 2 which are constructed to secure tube 4 to penis 12. More specifically, FIG. 6 shows a sideview of the condom 16, the inventive device 2, with the diaphragm 6. At the base end of the tube portion of this device and the innermost portion of the diaphragm is a narrow area 24 in width that is a slightly smaller circumference than the rest of the tubular shaft. This area of slightly smaller circumference also contains a thicker portion of the rubberlike material, this thicker and circumferentially smaller portion of the rubberlike shaft or tube would fit tighter on the erect penis to hold this preferred embodiment of the device in place during sexual intercourse and related activities.

Figure 7:
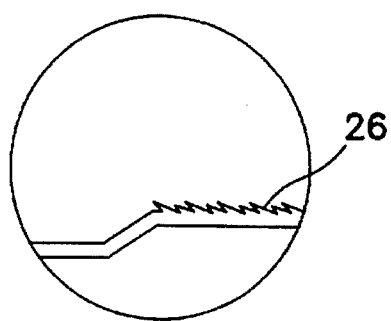
FIG. 7 is a Microscopic side cutaway view taken of a portion of FIG. 6.

FIG. 7 is a microscopic side cutaway view taken of a portion of FIG. 6. FIG. 7 in microscopic view shows the above mentioned ring portion with diagonally shaped teeth in the rubberlike material pointing outward toward the tubular end of the device and toward the head of the penis. These teeth would help the condom remain on the penis by creating an opposing motion or force to the drag of the condom off the penis when the penis is pulled out of the vagina repeatedly during sexual intercourse and related activities.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A flexible, protective shield worn at the base of a penis comprising:

a) a tubular member with a first and a second end, and b) a diaphragm with a through hole, where said diaphragm is attached to the first end of said tubular member with said hole generally aligned with the tubular axis such that the tubular member diaphragm combination retains a through hole, and where the diaphragm extends outward about radially from said axis, and c) said tubular member including a first area of adhesion, where said first area of adhesion is arranged and constructed to secure the tubular member to the penis and where said first area of adhesion is made of a thicker material and of a lesser diameter than the rest of said tubular member and further comprises small teeth directed toward the head or front end of the penis.

2. A shield as defined in claim 1 further comprising:

d) a condom which extends over the end of the penis and over the second end of the tubular member, and where said tubular member includes a second area of adhesion, said second area of adhesion arranged and constructed to secure the condom to the tubular member.

3. A shield as defined in claim 2 where said second area of adhesion is a ripple or a plurality of ripples, where each ripple provides an increased diameter over the diameter of the rest of said tubular member.

4. A flexible, protective shield worn at the base of a condom covered penis comprising:

a) a tubular member with a first and a second end, and said tubular member with first and second areas of adhesion, b) a diaphragm with a through hole, where said diaphragm is attached to the first end of said tubular member with said hole generally aligned with the tubular axis such that the tubular member diaphragm combination retains a through hole, and where the diaphragm extends outward generally radially from said axis, c) said first area of adhesion arranged and constructed to secure the tubular member to the penis, and said second area of adhesion arranged and constructed to secure the tubular member to the condom and where said first area of adhesion is made of a thicker material and of a lesser diameter than the rest of said tubular member and further comprises of teeth directed toward the head or front end of the penis.

* * * * *